US006254638B1

(12) United States Patent
Schouwenburg

(10) Patent No.: US 6,254,638 B1
(45) Date of Patent: Jul. 3, 2001

(54) VOICE PROSTHESIS WITH BIOMEDICAL SEALING ON THE CIRCUMFERENCE

(76) Inventor: Paul Ferdinand Schouwenburg, Grenslaan 4, nl-2111 Gh, Aerdenhout (NL)

( * ) Notice: Subject to any disclaimer, the term of this patent is extended or adjusted under 35 U.S.C. 154(b) by 0 days.

(21) Appl. No.: 09/068,748

(22) PCT Filed: Sep. 16, 1997

(86) PCT No.: PCT/NL97/00523

§ 371 Date: Sep. 20, 1999

§ 102(e) Date: Sep. 20, 1999

(87) PCT Pub. No.: WO98/10718

PCT Pub. Date: Mar. 19, 1998

(30) Foreign Application Priority Data

Sep. 16, 1996 (NL) .................................................. 1004042

(51) Int. Cl.[7] .................................................... A61F 2/20
(52) U.S. Cl. ............................................................. 623/9
(58) Field of Search ..................... 623/12, 23.64, 623/23.68, 9

(56) References Cited

U.S. PATENT DOCUMENTS

| 3,768,102 | * | 10/1973 | Kwan-Gett et al. | 3/1 |
| 4,968,294 | * | 11/1990 | Salama | 600/30 |
| 4,969,902 | * | 11/1990 | Ravo | 623/12 |
| 5,108,430 | * | 4/1992 | Ravo | 623/12 |
| 5,861,035 | * | 1/1999 | Griffth | 623/12 |
| 6,013,102 | * | 1/2000 | Pintauro et al. | 623/12 |

FOREIGN PATENT DOCUMENTS

| 222 509 | 5/1987 | (EP) . |
| WO 89/07916 | 9/1989 | (WO) . |

* cited by examiner

Primary Examiner—David J. Isabella
Assistant Examiner—Hieu Phan
(74) Attorney, Agent, or Firm—Sughrue, Mion, Zinn, Macpeak & Seas, PLLC

(57) ABSTRACT

A voice prosthesis has a tubular body with two ends and an internal through-cavity communicating the ends. There are external widened sections at the two ends, with a valve body at the first end to permit air to flow in only one direction. On an outer surface of the tubular body is an adaptation for sealing the tubular body to a wall of the hole between the esophagus and trachea. The adaptation, in particular, is one or more rings protruding from the outer surface at a position between the two ends. The rings protrude at an angle, causing them to be canted toward the opposite end.

19 Claims, 2 Drawing Sheets

VOICE PROSTHESIS WITH BIOMEDICAL SEALING ON THE CIRCUMFERENCE

The invention relates to a voice prosthesis intended to be positioned in a fistula in the wall between the oesophagus and the trachea, the trachea opening out in the throat via an orifice, which prosthesis comprises a tubular body, which is provided with an internal through-cavity and at both ends has external widened sections for holding the prosthesis with respect to the wall section adjoining the opening, as well as a valve body for closing off the through-cavity.

Voice prostheses of this kind are known. Examples which may be mentioned are the prostheses known from U.S. Pat. Nos. 4,435,853, 4,610,691 and EP-A-507,832. The valve body of these prostheses can be opened under the influence of an excess pressure in the trachea, so that speech can be imitated via the oesophagus and the pharynx. On the other hand, the valve has to close as soon as liquids or solid food move through the oesophagus, so that they cannot pass into the trachea.

Although the valve in the known prostheses is reasonably satisfactory, i.e. it is able to stop even liquids, the problem of choking has nevertheless been found to be difficult to avoid, due to the fact that drops of liquid still penetrate into the trachea. This is because in the long term the liquid has been found to be able to leak along the outside of the prosthesis. The cause of this problem is that the fistula in which the tubular body of the voice prosthesis is situated stretches over the course of time and thus becomes too wide to maintain the desired seal.

The result is that the voice prosthesis has to be removed. Then, it is necessary, by means of a surgical intervention, to restore the old state or, a few days after removal, to install a (larger) voice prosthesis. In both cases, admission to hospital is necessary, making these interventions rather expensive. These procedures are very onerous on the patient: during this time, it is not possible to speak, food is administered artificially by means of a stomach tube and the result of this treatment is frequently disappointing with a high risk of repeat occurrence. Consequently, external leakage is a difficult and expensive medical problem for users of voice prostheses.

As an additional factor, the abovementioned leakage problem occurs in approximately 10% of all patients. It is not possible to assess in advance which patients will be affected, meaning that any preventative measures will have to be taken for all patients, even in those cases in which there would not normally be any problems with leakage. Any solution to this problem therefore has to be simple and inexpensive, since a number of patients will never encounter leakage problems and additional measures are in fact superfluous in these cases.

However, it is known that after a relatively long period of time, the fistula in the tissue has an ever-increasing tendency to become stretched, so that even problem-free users can ultimately still encounter leakage. From a medical point of view, this is extremely undesirable since leakage can lead to liquids and thin food passing into the lungs, where they may cause serious lung complications.

The object of the invention is to provide a voice prosthesis which offers a better seal. This object is achieved in that the external surface of the tubular body, and/or the adjoining surfaces of the widened sections, comprises/comprise local elevations and/or recesses for sealing the prosthesis with respect to the wall section adjoining the opening.

The local elevations or recesses ensure a liquid-tight contact between the voice prosthesis and the wall region around the openings. On the other hand, in view of their relatively small dimensions, they do not lead to that area stretching, so that the seal does not lose its action even in the long term. Joining recesses or elevations to the voice prosthesis represents a comparatively simple adjustment, so that the cost price scarcely need be increased, thus bringing its use within the reach of the total population of patients.

The recesses or elevations may have all kinds of different forms. In the preferred embodiment, the tubular body comprises at least one encircling peripheral rib. A rib of this kind forms only a very localized widening of the tubular body, and will therefore not lead to the opening in which the prosthesis is positioned becoming stretched. On the other hand, the rib does bear reliably in a close-fitting manner against the wall of the opening, so that leakage can be reliably avoided. The tubular body may optionally have a plurality of ribs one behind the other.

Moreover, each peripheral rib, viewed in a section through the axis of the tubular body, may be directed obliquely with respect to the external surface of the tubular body. The oblique position of the rib provides an additional retention action for the voice prosthesis. This is all the more important in view of the fact that in the widened fistulae which cause leakage there is a considerable reduction in the retention action. This can lead to the voice prosthesis being lost in the trachea and/or the lungs.

The direction in which the rib points can be selected as a function of the type of voice prosthesis. In the case of voice prostheses which can be installed via the trachea orifice (front loading), it is preferably provided for each peripheral rib to be situated close to the widened section which is intended to be positioned in the oesophagus, and for it to be directed obliquely towards the other widened section.

Ribs of this kind can also be used in other prostheses, which are positioned via the mouth and the oesophagus.

The dimensions of the ribs are selected such that, on the one hand, they provide an adequate level of seal and, on the other hand, they do not lead to the opening becoming stretched. According to the invention, the height of each rib may preferably lie in the range from 1 mm to 3 mm.

In this connection, the thickness of the ribs is also important; the thickness may preferably lie in the range from 0.2 mm to 1 mm.

In the above text, seals in the form of a rib have been referred to. However, according to the invention the seal can also be obtained if the tubular body comprises at least one encircling peripheral groove.

Although the need for a reliable seal means that preference is given to elevations or recesses on the tubular body, nevertheless these could also be arranged on one of the flanges which are situated at the ends of the tubular body.

The invention will be explained in more detail below with reference to an exemplary embodiment depicted in the figures, in which.

Figure 1:
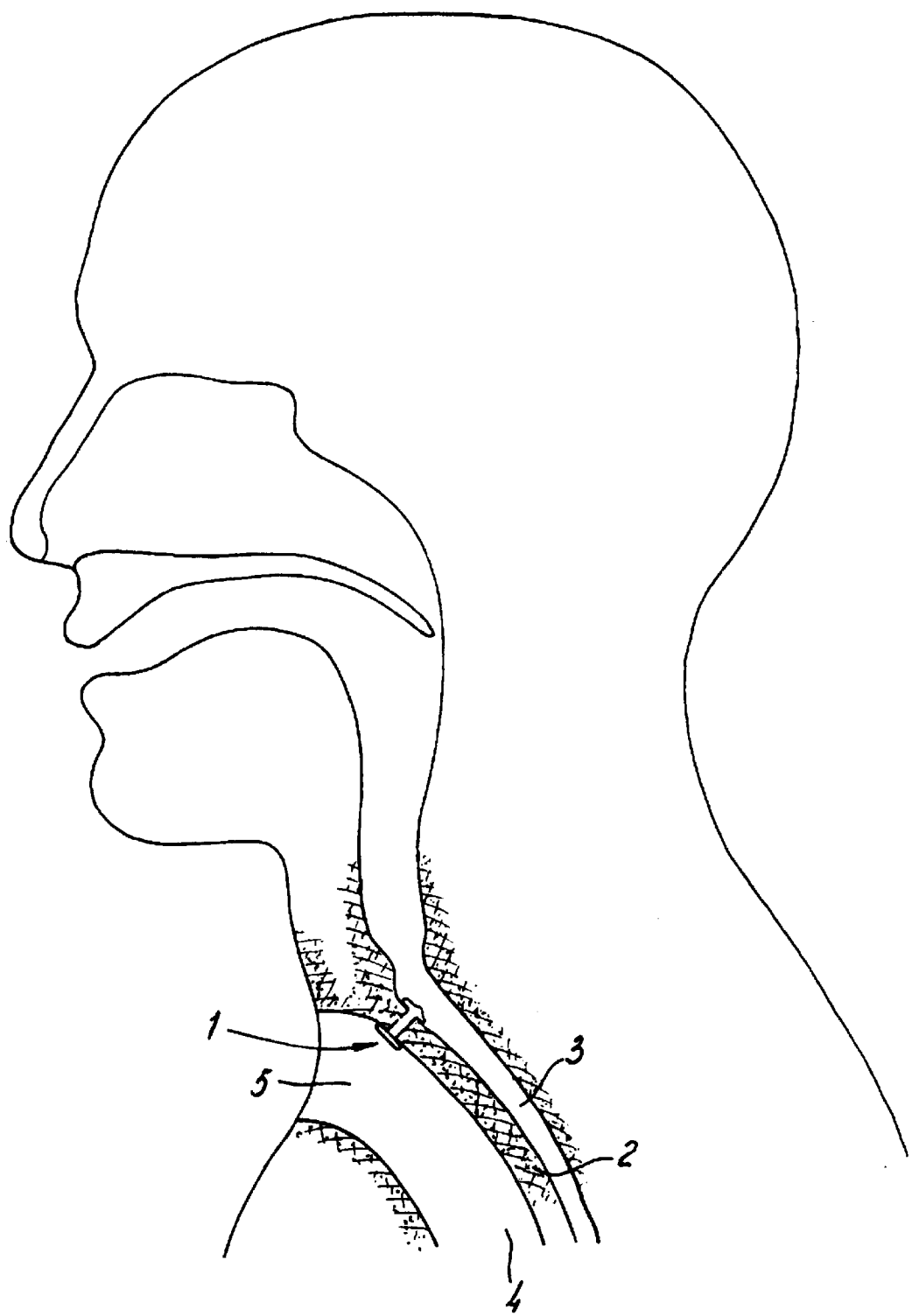
FIG. 1 shows the voice prosthesis according to the invention arranged in a patient.

In the position shown in FIG. 1, a voice prosthesis, which is denoted overall by 1, is arranged in the wall between oesophagus 3 and trachea 4. The trachea 4 opens out in the throat of the patient via orifice 5.

Figure 2:
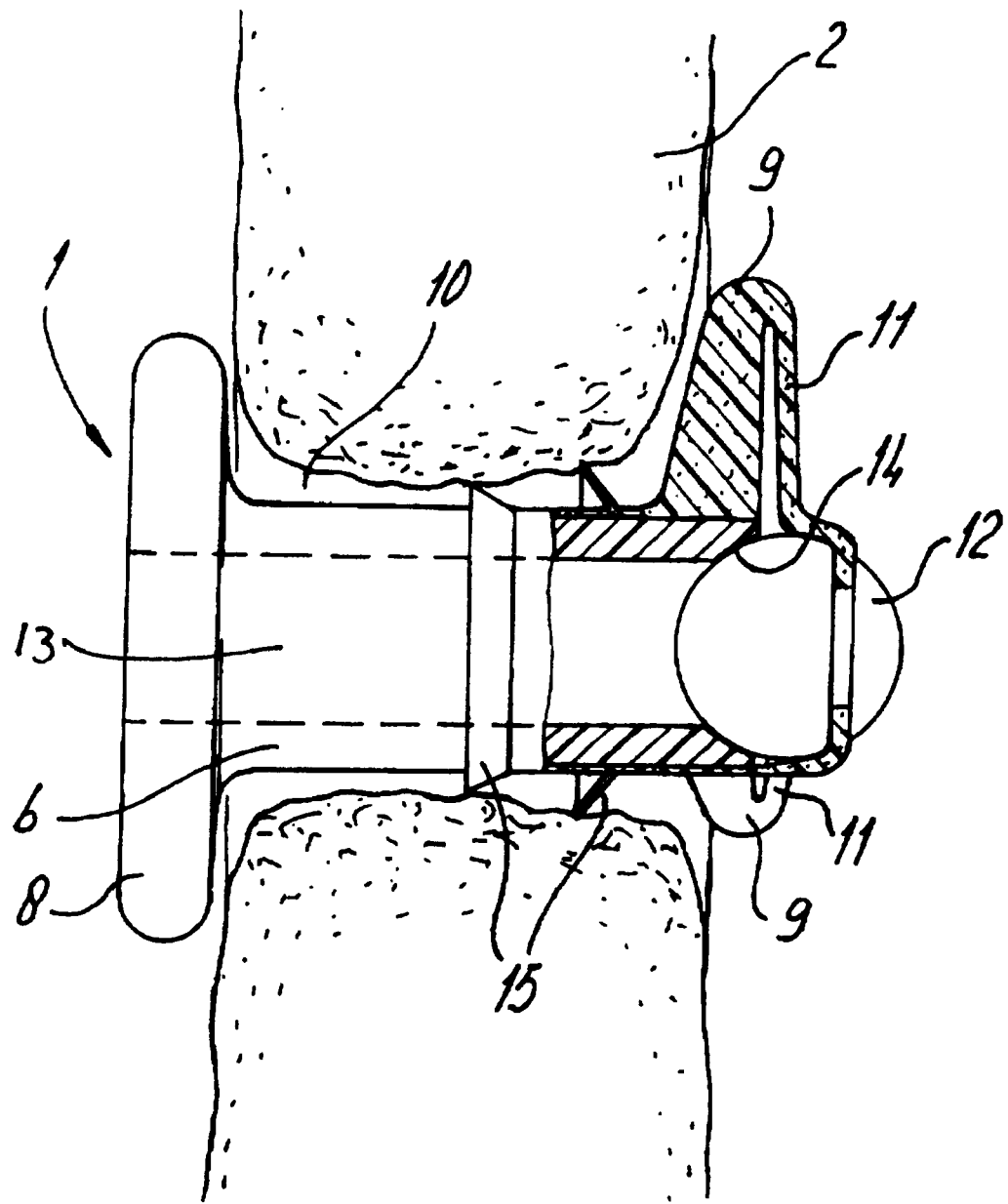
FIG. 2 shows the voice prosthesis in the deployed position, on a larger scale.

As can be seen in the larger-scale illustration of FIG. 2, the voice prosthesis 1 has a tubular section 6 as well as a flange 8 which bears against that side of the wall 2 which adjoins the trachea 4.

At the opposite end of the tubular body 6 are situated projections 9, which bear against that side of the wall 2 which adjoins the oesophagus 3. The voice prosthesis 1 is reliably held in place by means of flange 8 and projections 9. For a description of the way in which voice prosthesis 1 is arranged in the opening 10 of the wall 2, reference is made to the Dutch patent application 1,000,355, which is not a prior publication.

A spherical valve body 12 is attached to the outer ends of the projections 9 by means of elements 11. The projections 9 and elements 11 consist of flexible material, so that the valve body 12 can move with respect to the tubular body 6. This tubular body 6 has a through channel 13, which at its end formed by the valve body 12 forms a valve seat 14. The channel 13 is closed off by the resilient bearing of the valve body 12 against the seat 14, as provided by preloading in the projections 9 and elements 11. However, as soon as an excess pressure is built up in the trachea, the valve body 12 moves away from the seat 14, so that air can flow under pressure into the oesophagus 3, whereupon speech can be imitated.

As soon as liquids and food move through the oesophagus 3, the valve body 12 closes onto the seat 14, not only owing to the resilient pressure of projections 9 and elements 11, but also under the influence of the pressure which is exerted by the fluids or solid substances in the oesophagus 3.

In order also to prevent any drops of liquid from penetrating into the trachea 4 via the gap which could exist between the internal surface of the opening 10 and the external surface of the tubular body 6, ribs 15 are provided according to the invention. These ribs 15 extend to the internal wall of the opening 10, and provide a reliable seal, even if the internal wall of the opening 10 and the external wall of the tubular body 6 no longer bear against one another. In view of their small dimensions and their low contact area with the internal wall of the opening 10, the opening will not become stretched, with the result that the seal is ensured for a long time.

As depicted in FIG. 2, the ribs 15 are arranged near to the projections 9, and are directed slightly obliquely, so that they have a conical shape. Due to this location and oblique position, the ribs 15 also contribute to holding the voice prosthesis 1 in the opening 10 in the wall 2.

Although the invention has been described with reference to a specific type of voice prosthesis, as described in the abovementioned Dutch patent application 1,000,355, which is not a prior publication, the elevations, in the form of ribs 15, may nevertheless be employed in any type of voice prosthesis. A possible application which may be mentioned as an example is that of voice prostheses as are known from the above mentioned U.S. Pat. Nos. 4,435,853, 4,610,691 and EP-A-507,832.

What is claimed is:

1. A voice prosthesis intended to be positioned in a fistula in the wall between the esophagus and the trachea, the trachea opening out in the throat via an orifice, which prosthesis comprises a tubular body, which is provided with an internal through-cavity and at both ends has external widened sections for holding the prosthesis with respect to the wall section adjoining the fistula, as well as a valve body for closing off the through-cavity, wherein at least one of the external surface of the tubular body and the adjoining surfaces of the widened sections comprises local elevations sealing the prosthesis with respect to the wall section adjoining the fistula.

2. A voice prosthesis according to claim 1, the tubular body further comprising at least one encircling peripheral rib.

3. A voice prosthesis according to claim 2, further comprising each peripheral rib, viewed in section through the axis of the tubular body, being directed obliquely with respect to the external surface of the tubular body.

4. A voice prosthesis according to claim 2, further comprising each peripheral rib being situated close to the widened section which is intended to be positioned in the esophagus and being directed obliquely towards the other widened section.

5. A voice prosthesis according to claim 2, further comprising the height of each rib lying in the range from 1 mm to 3 mm.

6. A voice prosthesis according to claim 2, further comprising the thickness of each rib lying in the range from 0.2 mm to 1 mm.

7. A voice prosthesis according to claim 2, further comprising at least one of the ribs being formed by a separate ring which is clamped around the tubular body.

8. A voice prosthesis according to claim 1, further comprising at least one of the widened sections being a flange, which flange bears at least one encircling rib on its side facing towards the other widened section.

9. A voice prosthesis according to claim 1, further comprising at least one encircling peripheral groove on the tubular body.

10. A voice prosthesis, comprising:
   a tubular body with a first end and a second end, said first end and said second end together defining two ends of said tubular body;
   an internal through-cavity communicating said first end and said second end;
   external widened sections at said two ends;
   a valve body disposed at said first end of said tubular body, and operably disposed with respect to said tubular body to permit air to flow under pressure from said second end to said first end, and adapted to prevent said flow from said first end to said second end;
   said tubular body having an external outer surface between said two ends;
   said external outer surface having, between said two ends of said tubular body, means for sealing said tubular body to a wall of a hole between an esophagus and a trachea.

11. The voice prosthesis as set forth in claim 10, wherein said means for sealing comprises local elevations protruding from said external outer surface of said tubular body.

12. The voice prosthesis as set forth in claim 11, wherein said local elevations form one or more peripheral ribs encircling said external outer surface of said tubular body.

13. The voice prosthesis as set forth in claim 11, further comprising:
   said tubular body having an axis extending from said first to said second end;
   a plane substantially perpendicular to said axis;
   one of said one or more peripheral ribs protruding from said external outer surface at an angle of protrusion; and
   said angle of protrusion being oblique with respect to said plane.

14. The voice prosthesis as set forth in claim 13, wherein said angle of protrusion is such that said one of said one or more peripheral ribs is directed obliquely toward said second end of said tubular body.

15. The voice prosthesis as set forth in claim 12, wherein each of said peripheral ribs protrudes from said tubular body for a height of from 1 mm to 3 mm.

16. The voice prosthesis as set forth in claim 12, wherein each of said peripheral ribs has a respective thickness of from 0.2 mm to 1 mm.

17. The voice prosthesis as set forth in claim 12, wherein one of said one or more peripheral ribs is a separate ring disposed around said tubular body.

18. The voice prosthesis as set forth in claim 11, wherein one of said external widened sections comprises a flange bearing at least one encircling rib facing toward said first end of said tubular body.

19. The voice prosthesis as set forth in claim 10, wherein said means for sealing comprises at least one peripheral groove encircling said external outer surface of said tubular body.

\* \* \* \* \*